United States Patent
Mutsers

(10) Patent No.: US 7,498,055 B2
(45) Date of Patent: Mar. 3, 2009

(54) PROCESS FOR THE PREPARATION OF UREA GRANULES

(75) Inventor: Stanislaus Martinus Petrus Mutsers, Geleen (NL)

(73) Assignee: DSM IP Assets B.V., Heerlen (NL)

( * ) Notice: Subject to any disclaimer, the term of this patent is extended or adjusted under 35 U.S.C. 154(b) by 363 days.

(21) Appl. No.: 10/576,300

(22) PCT Filed: Oct. 15, 2004

(86) PCT No.: PCT/EP2004/011678

§ 371 (c)(1), (2), (4) Date: Apr. 19, 2006

(87) PCT Pub. No.: WO2005/049193

PCT Pub. Date: Jun. 2, 2005

(65) Prior Publication Data

US 2007/0059446 A1  Mar. 15, 2007

(30) Foreign Application Priority Data

Nov. 10, 2003 (EP) .................................. 03078522

(51) Int. Cl.
*C05C 9/00* (2006.01)
*B05D 7/00* (2006.01)
*C07C 273/02* (2006.01)

(52) U.S. Cl. .......................... 427/213; 71/28; 71/64.03; 564/63

(58) Field of Classification Search ...................... 71/28, 71/64.03; 564/63; 427/213
See application file for complete search history.

(56) References Cited

U.S. PATENT DOCUMENTS 3,117,020 A * 1/1964 Fabris et al. ................. 427/213

FOREIGN PATENT DOCUMENTS

GB  767 716  2/1957
GB  943 595  12/1963

OTHER PUBLICATIONS

International Search Report.

* cited by examiner

*Primary Examiner*—Wayne Langel
(74) *Attorney, Agent, or Firm*—Nixon & Vanderhye P.C.

(57) ABSTRACT

Process for the preparation of urea granules in a fluid-bed granulator, by using at least one feeding device to feed a urea melt in the form of a film to a fluidized bed of solid urea nuclei, upon which the nuclei grow by solidification of the urea melt on the nuclei, in which the amounts of biuret and water in the urea melt and in the urea granules fulfill the following relation $$\frac{b_m \cdot b_g}{w_m \cdot (w_m - w_g)} = 0.1 - 20$$

wherein
$b_m$=the % by weight of biuret in the urea melt
$b_g$=the % by weight of biuret in the urea granules
$w_m$=the % by weight of water in the urea melt
$w_g$=the % by weight of water in the urea granules.

18 Claims, 3 Drawing Sheets

U.S. PATENT DOCUMENTS

| | | | |
|---|---|---|---|
| 4,217,127 A * | 8/1980 | Kono et al. .................... 71/28 |
| 4,219,589 A * | 8/1980 | Niks et al. .................. 427/213 |
| 4,345,099 A * | 8/1982 | Young et al. ................. 564/63 |
| 4,501,773 A * | 2/1985 | Nioh et al. .................. 427/213 |
| 4,619,843 A | 10/1986 | Mutsers |
| 5,120,345 A * | 6/1992 | Kayaert et al. ................. 71/30 |
| 5,653,781 A * | 8/1997 | Kayaert et al. ................. 71/28 |
| 6,217,630 B1 * | 4/2001 | Chanen et al. ................ 71/28 |

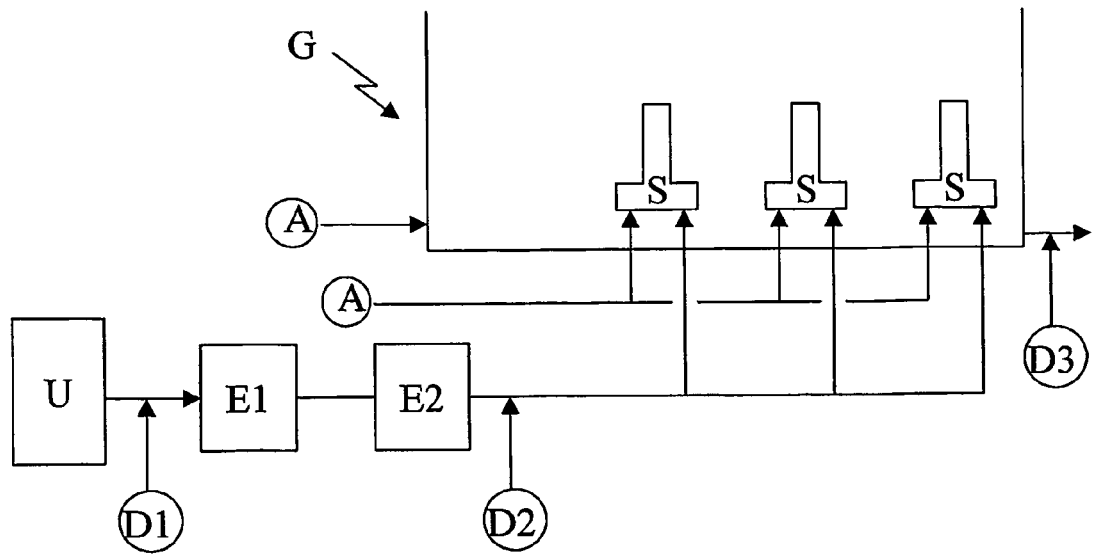
Figure 1/5
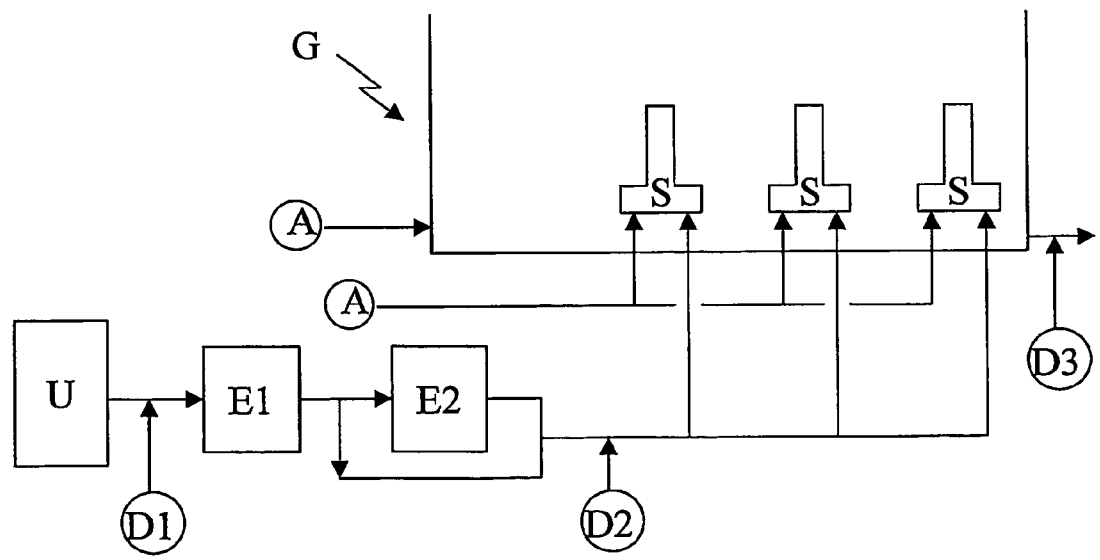
Figure 2/5

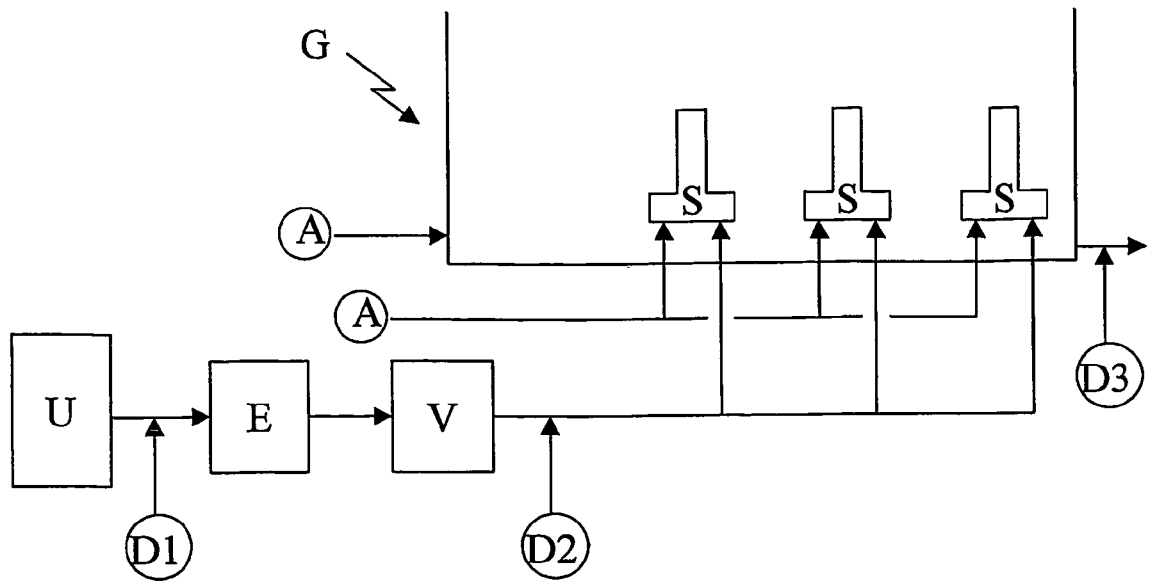
Figure 3/5
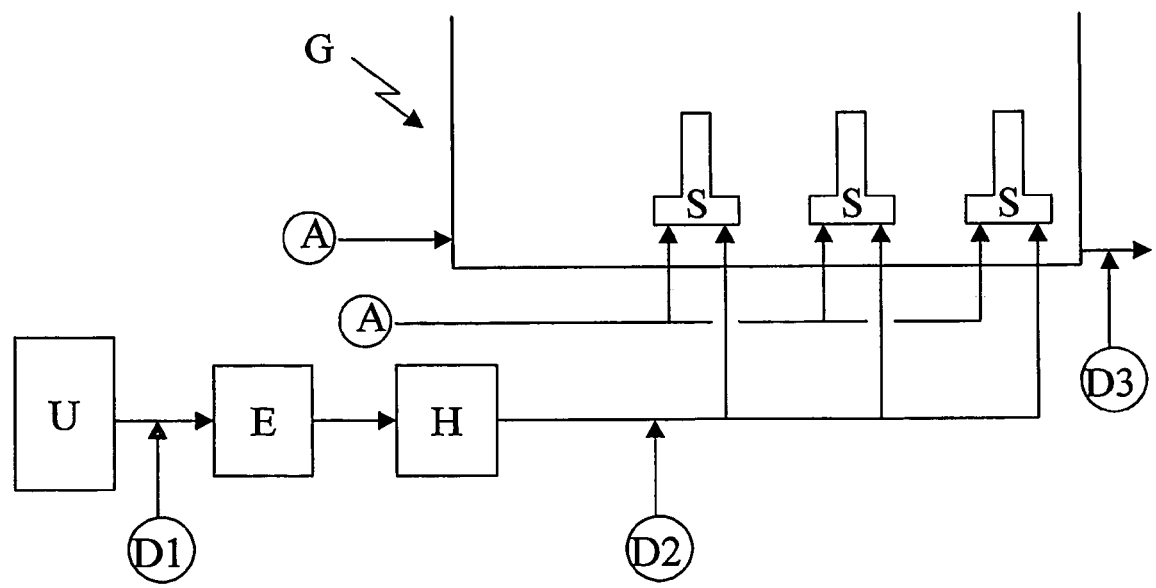
Figure 4/5

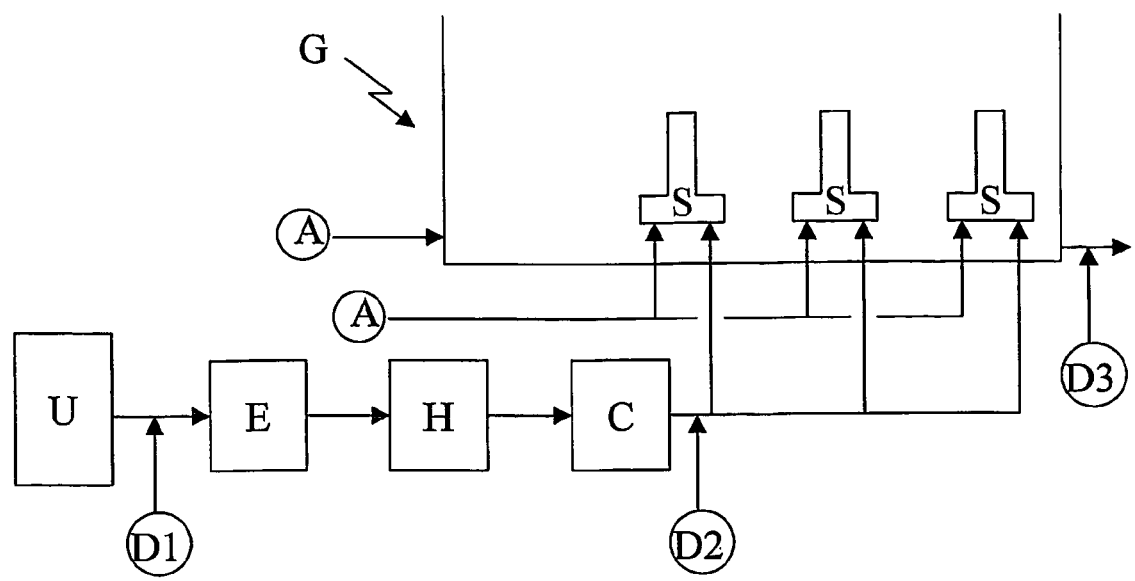
Figure 5/5

PROCESS FOR THE PREPARATION OF UREA GRANULES

This application is the U.S. national phase of international application PCT/EP2004/011678 filed 15 Oct. 2004 which designated the U.S. and claims benefit of EP 03078522.4, dated 10 Nov. 2003, the entire content of which is hereby incorporated by reference.

Various methods are known for the production of urea granules. In the past, the predominant method was prilling, in which a substantially anhydrous urea melt is sprayed from the top of a prilling column into a rising stream of air of ambient temperature in which the droplets solidify to form so-called prills. These prills have a relatively small maximum diameter and are mechanically rather weak.

Nowadays, urea granules having larger dimensions and better mechanical properties are produced by granulating a substantially anhydrous urea melt or of an aqueous urea solution in a fluidized bed, for instance as described in U.S. Pat. No. 4,619,843.

In this patent publication a process is described for the preparation of granules in a fluidized bed process by feeding a urea melt to a fluidized bed of solid urea nuclei, upon which the nuclei grow by solidification of the urea melt on the nuclei. The process is suitable not only for the preparation of urea granules, but also for the granulation of other materials such as sulphur and ammonium nitrate. In the fluidized bed feeding devices are used comprising a central channel from where the liquid material is supplied as a virtually closed, conical film and a channel concentric therewith through which a gas stream is supplied. The main advantage of this process is that it is low in energy consumption.

Besides urea, the urea melt that is fed to the fluidized bed contains water. The urea melt can, for instance, be obtained by concentrating an aqueous urea containing stream coming from a urea plant. This concentration takes place at high temperatures and/or low pressures. The concentrating conditions stimulate the formation of biuret. Biuret is an organic by-product that can be obtained during urea production. It has no adverse effects on human health or the environment. During fluid-bed granulation the weight % of biuret always shows a minor increase. The water present in the urea melt evaporates to a large extent during fluid-bed granulation of urea.

The presence of water in the urea melt used for fluid-bed granulation has some very important advantages.

First, concentration of the urea melt in an evaporator before feeding it to the fluidized bed is simpler and less energy consuming when some water is left in the urea melt. Second, the evaporation of the water in the fluidized bed improves the heat balance, so that less fluidizing air is needed for cooling. As a result thereof a smaller scrubbing section is needed to clean the fluidizing air.

The main disadvantage of the presence of water in the urea melt is the high concentration of granulation additives that needs to be present in the urea melt to be able to form urea granules out of the melt in a fluid-bed granulator. Granulation additives are expensive and hazardous to health and the environment. Examples of granulation additives used in urea granulation are formaldehyde, methylolurea, formurea and hexamethylenetetramine. The granulation additives are added to reduce dust formation during granulation, to obtain urea granules with satisfactory mechanical properties and to obtain free-flowing urea granules.

The present invention is based on extensive investigations aimed at reducing the concentration of granulation additives during granulation while at the same time maintaining or even improving the mechanical properties, such as crushing strength and caking tendency, and the free-flowing properties of the granules. Another aim was to reduce dust formation.

It has now surprisingly discovered that when during fluid-bed granulation the amounts of biuret and water in the urea melt and in the urea granules fulfill the following relation $$\frac{b_m \cdot b_g}{w_m \cdot (w_m - w_g)} = 0.1 - 20$$

wherein
$b_m$=the % by weight of biuret in the urea melt
$b_g$=the % by weight of biuret in the urea granules
$w_m$=the % by weight of water in the urea melt
$w_g$=the % by weight of water in the urea granules;

the required concentration of granulation additives can be greatly reduced. Granulation additives can even be absent during granulation.

During fluid-bed granulation the value of the above-mentioned relation is 0.1-20, preferably 0.1-10, most preferably 0.2-5. When the value of the above-mentioned relation is below 0.1 a large concentration of granulation additives is always necessary and a value of the relation above 20 leads to unacceptable high costs for energy consumption related to the evaporation section and/or to increased ammonia emission.

The amounts of water and biuret in the urea melt can be obtained by a large number of different methods. Examples of these methods are given below.

The amounts (given as weight percentages) of water and biuret in the urea melt can be obtained in and/or downstream of one or more evaporator(s) that are placed upstream of the feeding device. Preferably, two evaporators in series are used. All kinds of commercially available evaporators can be used; for instance VOP-type evaporators. Also, between the evaporator and the feeding device water, a water-rich urea solution or a biuret-rich stream can be added to the urea melt to influence the weight percentages of water and biuret in the urea melt.

The weight percentages of water and biuret in the urea melt can also be obtained in a vessel that is present between the evaporator and the feeding device. Biuret can be obtained in the urea melt when the temperature of the melt is higher than 130° C. The vessel can be kept at a temperature above 130° C. and the residence time of the urea melt can be chosen in such a way that a urea melt is obtained with the desired weight % of biuret.

The weight percentages of water and biuret in the urea melt between the evaporator and the feeding device can also be obtained in other ways, for instance by heating the piping used to feed the urea melt to the feeding device.

Preferably, the weight percentages of water and biuret in the urea melt are obtained by using two evaporators arranged in series, wherein part of the urea melt leaving the first evaporator being fed to the second evaporator and part of the urea melt leaving the first evaporator being combined with the urea melt leaving the second evaporator. This has the advantage that the amounts of biuret and water in the urea melt can be changed easily by varying the part of urea melt that flows from the first evaporator to the second evaporator.

The feeding device delivers the urea melt in the form of a film to a fluidized bed of solid urea nuclei, upon which the nuclei grow by solidification of the urea melt on the nuclei. The urea melt has to be fed to the fluidized bed in the form of a film in order to prevent dust formation. In principle, the film can have all kinds of configurations, but a virtually closed conical film is preferred.

The urea melt is introduced into the fluidized bed of nuclei from the bottom upwards with the aid of at least one feeding device provided with a central channel through which the urea melt is supplied and a channel concentric therewith through which a gas stream is supplied with a linear upward velocity higher than that of the fluidization gas. The gas stream creates a rarefied zone in the bed above the feeding device. After exiting the central channel the urea melt enters the rarefied zone. Before hitting the film, the gas stream sucks nuclei from the bed, entrains them and is thereby slowed down, so that both the film and the gas stream are deflected upon impact, and the entrained nuclei penetrate the film and are thereby moistened with a small amount of urea melt, which subsequently, in the rarefied zone, can solidify to such an extent that after exiting the rarefied zone the particles are sufficiently dry to prevent agglomeration.

A closed conical film can, in principle, be obtained in various ways. For example, the urea melt can be converted to a film with the aid of a tapered part at the end of the outlet channel. Preferably, the conical film is obtained by imparting a rotation to the urea melt. Of course, besides the rotational speed imparted to the material, the hydrostatic pressure on the urea melt is also important. In general, the urea melt is supplied under a hydrostatic pressure of 0.15 to 0.60 MPa, in particular 0.18 to 0.40 MPa. By preference, a feeding device provided with a rotation chamber is used.

It has been found that to obtain a smooth surface of the film the melt velocity should in general be at most 30 m/sec and preferably 10-25 m/sec.

The gas stream takes up nuclei and is thereby slowed down before hitting the film. This is preferably achieved by making the gas channel lead into the fluidized bed in a place lower than the central channel. In this way, the gas stream can entrain nuclei along some distance and impart a certain velocity to them before they hit the film. This so-called free distance can vary within wide limits, for example 0.5-5.0 cm. Preferably, a free distance of 1-4 cm is used.

In the present process, air is preferably used as the gas stream and is supplied with a velocity of at least 50 m/sec, in particular 50-400 m/sec, in general under a feed pressure of 0.11 to 0.74 MPa. The temperature of this gas stream can vary. In general, a gas stream is used which has a temperature that is about equal to that of the urea melt. The required amount of this gas stream is exceptionally low in the present invention. In general, a weight ratio of gas to urea melt of between 0.1 and 0.8, in particular between 0.2 and 0.6, is applied.

After exiting from the gas channel, the gas stream sucks nuclei from the bed and entrains them. The velocity of the gas stream thereby decreases, while the nuclei acquire a certain velocity, for example 0.1-10 m/sec.

When the film and the gas stream make impact, the nuclei entrained in the gas stream fly almost straight ahead, that is, through the film, on account of their mass. These nuclei are thereby moistened with a thin layer of urea melt, which completely or almost completely solidifies in the rarefied zone. The amount of urea melt taken up depends on, among other things, the film thickness and the particle diameter.

The gas stream not only transports particles but also serves to create the rarefied zone above the feeding device. This zone should be of sufficient height to allow the urea melt on the particles to solidify to a sufficient extent, for example about 30 cm, but on the other hand the surface of the bed should be prevented from breaking locally, in view of the risk of dust emission. These conditions are determined by the mass and velocity of the gas stream and the height of the bed, which is, for example, 40-100 cm.

As nuclei in the fluidized bed, in principle all kinds of pellets can be used, for example prills separately prepared from a portion of the urea melt to be sprayed, or from a melt obtained by melting the oversize fraction obtained after screening of the granulate. Preferably, as nuclei, granules are used which have been obtained during screening and/or crushing of a small portion of the granulate obtained from the bed. The average diameter of these nuclei may vary, partly depending on the nature of the material to be granulated and especially on the desired particle size of the product. The quantity of nuclei introduced may also vary.

The bed of nuclei is kept in a fluidized state by an upward-flowing gas, in particular air. This fluidization gas should have a minimum superficial velocity to ensure that the entire bed is kept in a fluidized state. On the other hand, this velocity should not be too high to prevent emission of urea fines.

The invention will be explained in detail with reference to the accompanying figures.

In FIGS. 1 to 5 different processes for the preparation of urea granules according to the invention are shown.

Figures D1-D3 are included as possible places for metering devices of granulation additives.

FIG. 1 U represents the urea process in which the urea melt was obtained. In this urea melt $b_m$ was 0.4 wt % and $w_m$ was 20 wt %. The urea melt was led to the evaporator (E1) to obtain a $b_m$ of 0.7 wt % and a $w_m$ of 5 wt % and thereafter to the evaporator (E2) to obtain a $b_m$ of 0.9 wt % and a $w_m$ of 1.3 wt %. After the evaporator the urea melt was led to the spraying devices (S) in the granulator (G). In the spraying devices the urea melt was sprayed together with the air stream (A). Fluidizing air was also fed to the granulator. Granules with a $b_g$ of 0.92 wt % and a $w_g$ of 0.1 wt % were obtained. The value of the quotient in the above-mentioned relation was 0.53.

In FIG. 2 a process for the preparation of urea granules was presented according to FIG. 1. A urea melt with a $b_m$ of 0.4 wt % and a $w_m$ of 20 wt % was led to the first evaporator. The urea melt that leaves the first evaporator had a $b_m$ of 0.7 wt % and a $w_m$ of 5 wt % and 75% of it was led to the second evaporator. After the second evaporator a stream with a $b_m$ of 0.9 wt % and a $w_m$ of 1.3 wt % was obtained. This stream of urea melt was combined with the rest of the urea melt leaving the first evaporator, resulting in a urea melt with a $b_m$ of 0.85 wt % and a $w_m$ of 2.2 wt %, which was led to the spraying devices. Granules with a $b_g$ of 0.88 wt % and a $w_g$ of 0.3 wt % were obtained. The value of the quotient in the above-mentioned relation was 0.18.

FIG. 3 represents a process for the preparation of urea granules according to FIG. 1 in which after the evaporator a vessel (V) was placed for further treatment of the urea melt. The urea melt that enters the evaporator had a $b_m$ of 0.4 wt % and a $w_m$ of 20 wt %. After the evaporator a urea melt was obtained with a $b_m$ of 0.7 wt % and a $w_m$ of 2 wt %. In the vessel the urea melt was kept at a temperature of 135° C. for 10 minutes, after which it was led to the spraying devices. The $b_m$ and $w_m$ values in the urea melt that was sprayed were 1.2 wt % and 2 wt %, respectively. Granules with a $b_g$ of 1.3 wt % and a $w_g$ of 0.3 wt % were obtained. The value of the quotient in the above-mentioned relation was 0.42.

FIG. 4 shows a process for the preparation of urea granules according to FIG. 1 in which after the evaporator a heating device (H) was placed for further treatment of the urea melt. The weight % of biuret and water in the urea melt that entered the evaporator are 0.4 and 20, respectively. After the evaporator a urea melt was obtained with a $b_m$ of 0.9 wt % and a $w_m$ of 1.0 wt %. In the heating device the urea melt was kept at a temperature of 150° C. for 1 minute, after which it was led to the spraying devices. The $b_m$ and $w_m$ values in the urea melt that was sprayed are 2.5 wt % and 1.0 wt %, respectively. Granules with a $b_g$ of 2.6 wt % and a $w_g$ of 0.1 wt % were obtained. The value of the quotient in the above-mentioned relation was 7.2.

FIG. 5 shows a process for the preparation of urea granules according to FIG. 1 in which after the evaporator a heating device (H) and a cooler (C) were placed for further treatment of the urea melt. The weight % of biuret and water in the urea melt that enters the evaporator were 0.4 and 20, respectively. After the evaporator a urea melt with a $b_m$ of 0.8 wt % and a $w_m$ of 1.5 wt % was obtained. In the heating device the urea melt was kept at a temperature of 160° C. for 30 seconds, after which it was led to the cooler. In the cooler the urea melt was kept at a temperature of 135° C. for 10 seconds, after which it was led to the spraying devices. In the urea melt that was sprayed $b_m$ was 2.2 wt % and $w_m$ was 1.5 wt %. Granules with a $b_g$ of 2.3 wt % and a $w_g$ of 0.2 wt % were obtained. The value of the quotient in the above-mentioned relation was 2.59.

EXAMPLES

The mechanical properties of the granulate produced in the granulator are characterized by a number of quality parameters. One such quality parameter is the crushing strength of a granule, defined as the pressure at which a granule breaks down into fine particles. The crushing strength of a granule is of importance in the handling and storage of the urea product between the manufacturer's plant and the end user. In order to assure that the product conforms to user expectations (such as easy handling, good spread-ability, low/no losses in the application) at the end-user, too, the crushing strength of the granulate as produced in the manufacturer's plant should be more than 2 MPa, and preferably more than 3 MPa. It has now been found that the crushing strength of the produced granulate can be influenced by modifying the parameters in the above-mentioned relation. At a value of the above-mentioned relation above 0.1 granulate with a good crushing strength can be obtained with considerably lower, or even no, metering of the above-mentioned granulation additives.

Example A

A fluid bed granulator including a feeding device that fed the urea melt in the form of a virtually closed conical film was used in a process set-up as shown in FIG. 1. A urea melt having a $b_m$ of 0.9 wt % and a $w_m$ of 1.3 wt % was supplied to this feeding device. The values for the $b_g$ en $w_g$ in the granules were 0.92 wt % and 0.1 wt %. The value of the relation was 0.52. Without any formaldehyde having been metered, the crushing strength of the urea granules produced had an acceptable value of 3.0 MPa. After metering of 0.2 wt % of formaldehyde (relative to the total amount of melt supplied to the feeding device), the crushing strength of the urea granules increased to 4.2 MPa.

Comparative Experiment 1

Urea granules were prepared according to the same process as described in Example A.

Using only evaporator E1 for the treatment of the urea melt, a urea melt with a $b_m$ of 0.7 wt % and a $w_m$ of 5.0 wt % was supplied to the feeding device. Granules were obtained with a $b_g$ of 0.7 wt % and a $w_g$ of 1.0 wt %. The value of the relation was 0.024. 0.5 wt % of formaldehyde (relative to the total melt supply to the feeding device) was added via metering device D1. Urea granules with an unacceptable crushing strength of 0.7 MPa were obtained. When the metering of formaldehyde was stopped, the crushing strength of the urea granules dropped to the even lower value of 0.5 MPa.

Another important mechanical property of the granulate produced is its caking tendency. A non-caking, free flowing product is of importance to ensure easy handling and minimum spillage of the product during transport, as well as at its final application. The most common final application of urea is fertilizer. In most countries, fertilizer is nowadays spread over the land by rolling mechanical devices. It is very important that in these mechanical devices the urea is free flowing and is free of lumps. Lumps in, or non-free flowing behavior of the urea granulate, would result in uneven distribution of the fertilizer over the land, with a negative influence on the crop-yield in those land area's where a lower than average dosing of fertilizer is applied. The caking tendency of urea can, for example, be measured in a test in which a sample of the granulate is stored for a certain time under a specified pressure. The pressure that is required to break the sample after this storage is a measure of the caking tendency of the granulate. The higher this breaking pressure, the higher the caking tendency of the product. In general, the caking tendency should be lower than 0.8 bar in order to ensure that the application of the fertilizer at the end-user will be trouble free.

It is well known that the caking tendency of urea granulate can be reduced by adding granulation additives. It is also known that the caking tendency of urea granulate can be reduced by covering the surface of the granulate with surface-active components. For this purpose sometimes aqueous solutions of a saponifier (such as alkyl sulphonate or alkyl sulphate) are sprayed over the surface of the urea granulate. A disadvantage of this kind of surface protection of the granulate is the high cost of these additives.

It has now been found that the caking tendency of urea granulate can also be influenced by the value of the above-defined relation between the values of biuret and water. By choosing the right values for biuret and water a granular product with good to excellent non-caking behavior can be obtained without metering the above-mentioned additives, or with greatly reduced quantities of additives.

Example B

A fluid bed granulator, that included, applying a feeding device that fed the urea melt in the form of a virtually closed conical film was used in a process set up as given in FIG. 5. With this feeding arrangement a urea melt with a $b_m$ of 2.2 wt % and a $w_m$ of 1.5 wt % could be obtained. In the granules the $b_g$ was 2.3 wt % and the $w_g$ was 0.2 wt %. The value of the relation was 2.59. The caking tendency of the urea granules had an acceptable value (0.4 bar). After adding only 0.05% of an aqueous solution of ethyl-hexyl sulphate via dosing device D3, the caking tendency of the urea granules had an excellent value of <0.1 bar. In this way the handling of a toxic formaldehyde solution could be avoided, whilst the cost of the expensive ethyl-hexyl sulphate metering was halved compared to comparative experiment 2.

Comparative Experiment 2

The evaporation section between the urea plant and the feeding device to the granulator was modified in the way illustrated in FIG. 1 with only one evaporator. A urea melt having a $b_m$ of 0.7 wt % and a $w_m$ of 5.0 wt % was supplied to this feeding device. The values of $b_g$ and $w_g$ were respectively 0.7 wt % and 1.0 wt %. The value of the relation was 0.024. 0.5 wt % of formaldehyde (relative to the total melt supply to the feeding device) was added via metering device D1. 0.1 wt % (relative to the total melt supplied to the feeding device) of an aqueous solution of ethyl-hexyl sulfate was added to the granulate via metering device D3. Urea granules with a good non-caking behavior were obtained (caking tendency <0.1 bar). When the metering of formaldehyde and of ethyl-hexyl sulphate was stopped, the caking tendency of the urea granules appeared to be fully unacceptable (caking tendency 2 bar).

The invention claimed is:

1. Process for the preparation of urea granules in a fluid-bed granulator comprising the steps of:
   (a) feeding a film of a urea melt from at least one feeding device to a fluidized bed of solid urea nuclei, and
   (b) bringing the solid urea nuclei into contact with the film of the urea melt so as to cause the nuclei to grow by solidification of the urea melt thereon to form the urea granules, wherein
   the urea melt and the urea granules contain amounts of biuret and water which fulfill the following relation $$\frac{b_m \cdot b_g}{w_m \cdot (w_m - w_g)} = 0.1 - 20$$

wherein
$b_m$=the % by weight of biuret in the urea melt
$b_g$=the % by weight of biuret in the urea granules
$w_m$=the % by weight of water in the urea melt
$w_g$=the % by weight of water in the urea granules.

2. Process according to claim 1, wherein the value of the quotient in the relation is 0.1-10.

3. Process according to claim 1, wherein value of the quotient in the relation is 0.2-5.

4. Process according to claim 1, wherein the urea melt is obtained in and/or downstream of an evaporator.

5. Process according to claim 1, wherein the urea melt is obtained by using two evaporators arranged in series, with part of the urea melt leaving the first evaporator being fed to the second evaporator and part of the urea melt leaving the first evaporator being combined with the urea melt leaving the second evaporator.

6. Process according to claim 1, which comprises adding water to the urea melt between the evaporator and the feeding device to obtain the urea melt.

7. Process according to claim 1, which comprises adding a biuret-rich stream between the evaporator and the feeding device to obtain the urea melt.

8. Process according to claim 1, wherein a vessel is present between the evaporator and the feeding device in which the urea melt is obtained.

9. Process according to claim 1, wherein the temperature of the urea melt is raised between the evaporator and the feeding device to obtain the urea melt.

10. Process according to claim 1, wherein step (a) is practiced by feeding the urea melt to the fluidized bed in the form of a virtually closed conical film.

11. Process according to claim 1, wherein the at least one feeding device comprises a central conduit for feeding the urea melt to the fluid-bed granulator and a conduit concentric with the central conduit through which a gas stream is delivered.

12. Process according to claim 1, wherein the urea melt has a velocity when exiting a central channel of the at least one feeding device of between 10 and 25 m/s.

13. Process according to claim 1, wherein the fluidized bed is fluidized by a gas stream, and wherein the urea melt is fed to the fluid-bed in a higher place than the gas stream.

14. Process according to claim 1, wherein the fluidized bed is fluidized by a gas stream, and wherein the gas stream has a velocity of 50-400 m/s and a feed pressure of 0.11-0.74 MPa.

15. Process according to claim 1, wherein the fluidized bed is fluidized by a gas stream, and wherein a weight ratio of the gas stream to the urea melt is 0.2-0.6.

16. Process according to claim 1, wherein the fluid-bed granulator is fluidized by a gas stream which causes the nuclei to penetrate the film and to thereby be moistened with the urea melt.

17. Process according to claim 16, wherein step (a) includes forming a substantially closed conical film of the urea melt from the at least one feeding device.

18. Process according to claim 17, wherein step (a) includes imparting rotation to the urea melt to obtain the substantially closed conical film thereof.

* * * * *